United States Patent
Nicolle et al.

(10) Patent No.: US 9,857,165 B2
(45) Date of Patent: Jan. 2, 2018

(54) SYSTEM FOR CHARACTERIZING THE PHYSIOLOGICAL STATE OF PLANTS AND CORRESPONDING METHOD

(71) Applicant: E.RE.C.A—INGENIERIE EN ELECTRONIQUE ET INFORMATIQUE INDUSTRIELLE, Vaulx en Velin (FR)

(72) Inventors: Serge Jacques Nicolle, Bron (FR); Sebastien Debuisson, Allemant (FR)

(73) Assignee: E.RE.C.A.—INGENIERIE EN ELECTRONIQUE ET INFORMATIQUE INDUSTRIELLE, Vaulx en Velin (FR)

( * ) Notice: Subject to any disclaimer, the term of this patent is extended or adjusted under 35 U.S.C. 154(b) by 56 days.

(21) Appl. No.: 14/784,773

(22) PCT Filed: Apr. 18, 2014

(86) PCT No.: PCT/FR2014/050954
§ 371 (c)(1),
(2) Date: Oct. 15, 2015

(87) PCT Pub. No.: WO2014/170620
PCT Pub. Date: Oct. 23, 2014

(65) Prior Publication Data
US 2016/0084636 A1    Mar. 24, 2016

(30) Foreign Application Priority Data
Apr. 18, 2013 (FR) .................................... 13 53542

(51) Int. Cl.
*G01B 11/02* (2006.01)
*G01B 11/08* (2006.01)
(Continued)

(52) U.S. Cl.
CPC .............. *G01B 11/08* (2013.01); *A01G 17/00* (2013.01); *G01B 5/0035* (2013.01);
(Continued)

(58) Field of Classification Search
CPC .... G01N 33/46; G01B 11/08; G01B 11/0035; G01B 11/2433
See application file for complete search history.

(56) References Cited

U.S. PATENT DOCUMENTS

2006/0272201 A1* 12/2006 Pellenc ................ A01B 69/001
47/1.01 R
2007/0044445 A1* 3/2007 Spicer .................... G01B 11/24
56/10.1

FOREIGN PATENT DOCUMENTS

EP    0974262 A1    1/2000

OTHER PUBLICATIONS

International Search Report and Written Opinion for PCT/FR2014/050954.

* cited by examiner

*Primary Examiner* — Michael P Stafira
(74) *Attorney, Agent, or Firm* — McClure, Qualey & Rodack, LLP

(57) ABSTRACT

The invention concerns a system (1) for characterizing the physiological state of woody plants (2, 3) with branches grown in rows, such as vine plants, said system (1) including a vehicle (10) designed to move between said rows, a geolocation device (14) and a processing unit (15), and being characterized in that it includes a sensor (16) including a light source (17) designed to emit a light beam (18) and a light receiver (19), said light beam (18) being able to intersect the branches, as the vehicle (10) moves forward, said light beam (18) having a dimension (L) greater than the diameter (D) of the thickest of the branches in said row (6),
(Continued)

said light beam (18) projecting, onto said light receiver (19), a shadow (20A, 20B) from which the processing nit (15) determines the diameter (D1, D2) of the branch (2A, 2B) in question.

15 Claims, 2 Drawing Sheets

(51) Int. Cl.
  *A01G 17/00* (2006.01)
  *G01N 33/46* (2006.01)
  *G01B 5/00* (2006.01)
  *G01B 11/24* (2006.01)
  *H04N 5/372* (2011.01)
(52) U.S. Cl.
  CPC ......... *G01B 11/2433* (2013.01); *G01N 33/46* (2013.01); *H04N 5/372* (2013.01); *G01B 2210/46* (2013.01)

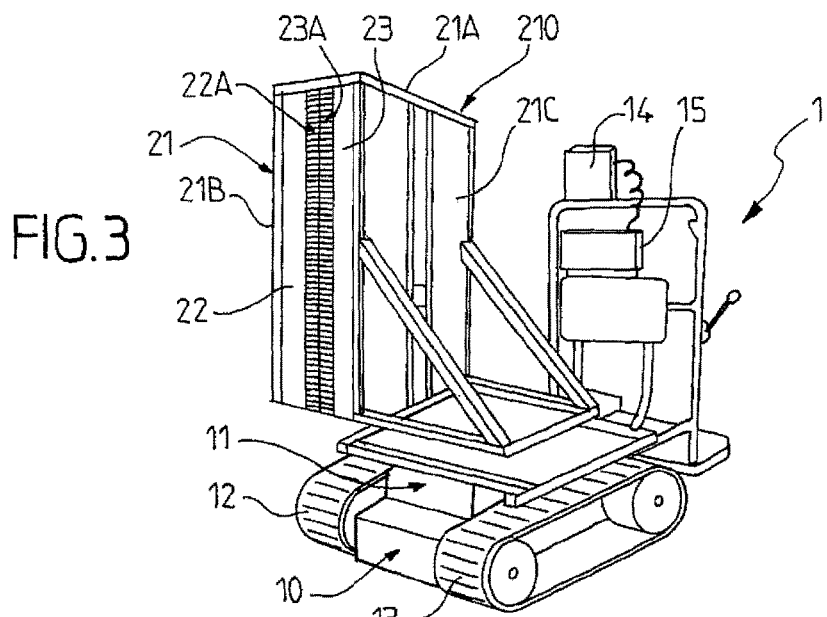
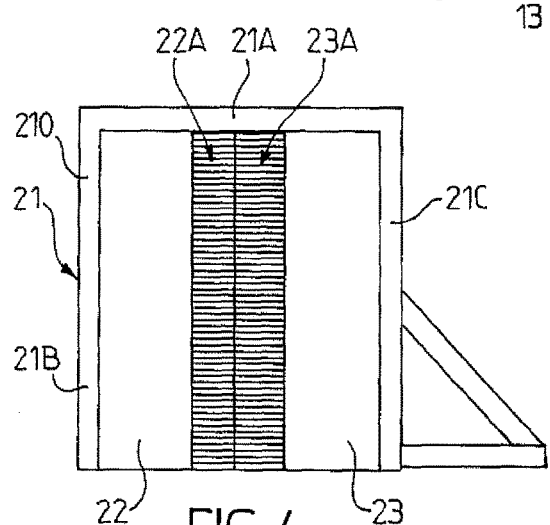
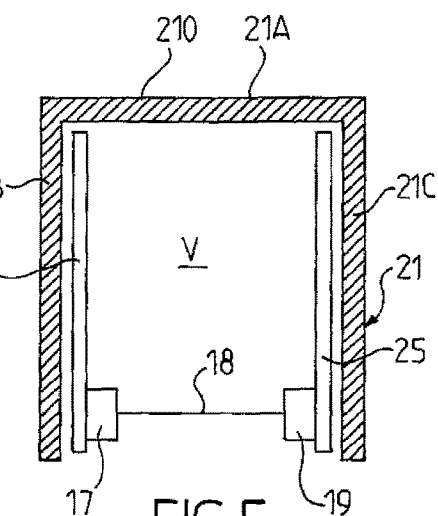
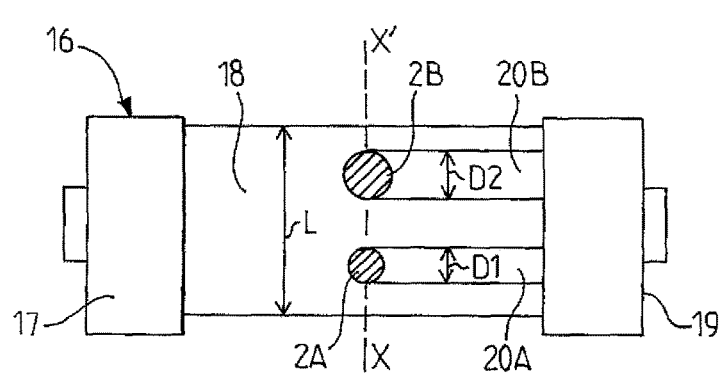

SYSTEM FOR CHARACTERIZING THE PHYSIOLOGICAL STATE OF PLANTS AND CORRESPONDING METHOD

TECHNICAL FIELD

The present invention relates to the general technical field of agricultural machinery, and more precisely, to the sector of proxidetection tools allowing to collect data representative of the physiological state of plants and in particular plants grown in rows, such as vine plants.

The invention more particularly relates to a system for characterizing the physiological state of woody plants with branches grown in rows, of the vine or fruit-tree type, said system comprising a vehicle designed to progress between said rows along a direction of progression, and also comprising a geolocation device on-board said vehicle, as well as a processing unit.

The invention also relates to a method for characterizing the physiological state of woody plants with branches grown in rows, of the vine or fruit-tree type.

PRIOR ART

The supply of inputs (including in particular phytosanitary or fertilizer treatments) and the implementation of various cultural operations, as for example operations of pruning or of vegetal invasion management, are common practices in wine growing. These supplies and cultural operations are still today generally implemented uniformly on the concerned plots, even as there yet very often exists a spatial variability within a same plot or between the plots, which would justify a non-uniform, differentiated implementation of the above-mentioned input supplies and cultural operations.

In order to be able to implement such a differentiated approach, it is required to be able to accede to objective parameters characteristic of the potential physiological variability of the vine.

For that purpose, it is known to implement remote sensing methods, which are based on the use of vegetation sensor on-board aircrafts (planes, drones or satellites). The remote sensing techniques allow to rapidly obtain measurements of parameter over large surfaces.

However, due to the discontinuous character of the vine and of the level of resolution of the known remote sensing systems, the information obtained is generally too rough to produce an optimum result.

It is also known to use proxidetection technologies based on the implementation of sensors, which are this time on-board terrestrial vineyard machines. The proxidetection technologies currently known generally allow to accede to more accurate information than that obtained by remote sensing, but at the price of a generally longer time of acquisition. The objective of proxidetection is hence to automatically collect a great series of measurements over the whole plot, so as to have the most exhaustive information possible regarding the potential physiological variability of the vine.

Different proxidetection tools are already available, among which a device available under the commercial name "Greenseeker NDVI®", which is based on the use of a sensor using the optical properties of the chlorophyll as regards the absorption and emission of light. The sensor in question is an active sensor able to generate a light in the red and the near infrared regions towards the plant, and a photodiode to measure the reflected light. From these measurements, the sensor calculates the NDVI ("Normalised Difference Vegetation Index") corresponding to a ratio between the red and the near infrared, varying between −1 and 1. This material, although being wholly satisfactory, has nevertheless some drawbacks. In particular, the technology implemented does not allow to measure a concentration of chlorophyll: the sensor indeed provides a saturated value from the lowest contents of chlorophyll observable in the vine leaves. It further turns out that the NDVI provided by this material is directly linked to the foliage porosity. In certain situations (low vegetation thickness vineyard, such as the Champagne vineyard), the porosity is directly linked to the total leaf surface (generally referred to as TLS). The NDVI tracking over time and space hence allows to comprehend the foliage growing as well as the TLS variability within the plot. However, as soon as the foliage thickens, the sensor tends to be saturated and does no longer allow to assess the foliage density (thickness). The foliage quantity can of course be more or less correlated with a set of agronomic parameters (yield, must characteristics . . . ) but it is not certain that the correlations are necessarily stable over time and space, it being further understood that the cultural practices such as topping or the pruning type modify the response of the sensor. Eventually, this material allows first, with the limitations exposed hereinabove, to characterize the vegetative expression, but does not allow in particular to accede to other parameters that could prove to be important, as the vitality.

Moreover, another material is known, available under the commercial name "Multiplex Force A®", which is based on the implementation of a multi-parameter optical sensor using the fluorescent properties of certain families of molecules present in the vine leaves and grapes to estimate their content. The data coming from this material may be more or less correlated with a set of agronomic parameters (yield, must characteristics . . . ) but these correlations are here again not necessarily stable over time and space. This material hence allows to estimate the metabolism of the leaves and grapes, but here again does not allow to assess other significant parameters, as the vine vitality.

Eventually, the known materials briefly described hereinabove allow to perform measurements that may be linked to criteria characterizing the vegetative expression or the metabolism. However, these materials are above all based on measurements on leaves and grapes. Hence, they do not allow to estimate a potential in vegetation beginning, for example during the winter period, before the leaves grow.

In order to determine this potential during the period of vegetative rest, a motorized device has been experimentally developed, which carries a digital camera modified to take a picture every four seconds on a vine plot. The so-obtained images are coupled to measurements of geographic positions, then processed and analysed to obtain information regarding not only the vegetative expression but also the vine vitality. Such a device, although allowing to obtain interesting results, has nevertheless certain drawbacks as regards both the measurement accuracy and the difficulty to process the volume of collected data.

Finally, there also exists in the prior art still another device allowing to measure the vitality of the vegetation and based on a measurement of vine shoot diameter obtained by determining the time taken by a given vine shoot to cut successively two light beams arranged parallel to each other and remote from each other, and by combining this measured duration with the speed of progression of the device in the vegetation row. This device has however serious drawbacks too. In particular, the assessment of the vitality it allows to obtain is dependent on the knowledge of the device progression speed, which is difficult to control with accuracy and which may vary as a function of the nature of the plot ground, which may be more or less uneven. The necessity to know accurately the speed of progression implies not only to use very reliable and accurate tachometric means, hence potentially expensive, but moreover has a negative influence on the volume of data to be processed (which must necessarily include the speed). Moreover, this known device does not allow to establish accurately an accurate map of the variability of the physiological state of the plants of the concerned plot.

EXPOSURE OF THE INVENTION

Consequently, the objects assigned to the present invention aim to remedy the above-mentioned drawbacks of the prior art and to propose a new system for characterizing the physiological state of woody plants with branches grown in rows, which allows to obtain accurate measurements, with an excellent spatial resolution, in a particularly rapid, reliable and economical manner.

Another object of the invention aims to propose a new system for characterizing the physiological state of woody plants with branches grown in rows, which allows to accede in a particularly simple, rapid and reliable manner to the wood biomass of a given plot.

Another object of the invention aims to propose a new system for characterizing the physiological state of woody plants with branches grown in rows, which allows to obtain rapidly a particularly fine and accurate map of the variability of physiological parameters of woody plants grown on a given plot.

Another object of the invention aims to propose a new system for characterizing the physiological state of woody plants with branches grown in rows, which is of particularly simple and robust construction, and adapted to any nature of ground.

Another object of the invention aims to propose a new system for characterizing the physiological state of woody plants with branches grown in rows, which is particularly accurate.

Another object of the invention aims to propose a new system for characterizing the physiological state of woody plants with branches grown in rows, which is based on the implementation of simple, reliable and cheap standard components.

Another object of the invention aims to propose a new system for characterizing the physiological state of woody plants with branches grown in rows, which can be used in any weather, and in particular in very sunny weather.

Another object of the invention aims to propose a new system for characterizing the physiological state of woody plants with branches grown in rows, whose construction is adjustable so as to be adaptable to the morphological characteristics of the concerned rows of woody plants.

Another object of the invention aims to propose a new system for characterizing the physiological state of woody plants with branches grown in rows, whose construction is based on the implementation of a minimum of known and proven components.

Another object of the invention aims to propose a new method for characterizing the physiological state of woody plants with branches grown in rows, which allows to obtain accurate measurements, with an excellent spatial resolution, in a particularly rapid, reliable and economical manner.

Another object of the invention aims to propose a new method for characterizing the physiological state of woody plants with branches grown in rows, which is based on the implementation of standard components.

Another object of the invention aims to propose a new method for characterizing the physiological state of woody plants with branches grown in rows, which allows to accede in an extremely simple and rapid manner to an assessment of the wood biomass of a given plot.

Another object of the invention aims to propose a new method for characterizing the physiological state of woody plants with branches grown in rows, which allows to comprehend in a particularly simple, rapid and cheap manner the potential of vegetative development of the woody plants grown in a given plot for a given year.

The objects assigned to the invention are achieved by means of a system for characterizing the physiological state of woody plants with branches grown in rows, of the vine or fruit-tree type, said system comprising a vehicle designed to progress between said rows along a direction of progression, and also comprising a geolocation device on-board said vehicle, as well as a processing unit, said system being characterized in that it comprises a sensor including a light source designed to emit a light beam and a light receiver, said light sources and receivers being mounted on said vehicle in such a way to be able be arranged on either side of a row, so that said light beam can intersect, as the vehicle progresses along said row, branches belonging to the woody plants of said row, said light beam having, in the direction of progression, a dimension that is substantially greater than the diameter of the thickest of the branches on said row, so that the interposition of a branch between the light source and receiver cuts only partially said light beam and hence projects on said light receiver a shadow from which the processing unit determines the local diameter of the concerned branch, said processing unit being further designed to associate with said local diameter of the concerned branch information of geolocation of said branch coming from the geolocation device.

The objects assigned to the invention are also achieved by means of a method for characterizing the physiological state of woody plants with branches grown in rows, of the vine or fruit-tree type, said method being characterized in that it comprises the following steps:

a sensor, including a light source designed to emit a light beam and a light receiver, is associated with a row, so that said light sources and light receivers are arranged on either side of said row;

said sensor is displaced along said row along a direction of progression so that said light beam can intersect, as the sensor progresses along said row, branches belonging to woody plants of said row, said light beam having, in the direction of progression, a dimension that is substantially greater than the diameter of the thickest of the branches in said row, so that the interposition of a branch between the light source and receiver cuts only partially said light beam and hence projects on said light receiver a shadow from which the local diameter of the concerned branch is determined;

information of geolocation of said concerned branch is associated with said local diameter.

BRIEF DESCRIPTION OF THE DRAWINGS

Other features and advantages of the invention will be better understood from the reading of the following description, with reference to the appended drawings, given only by way of illustrative and non-limitative example, in which:

FIG. 3 illustrates, in a schematic perspective view, an exemplary embodiment of a system according to the invention.

FIG. 4 illustrates, in a schematic elevation view, a detail of the system illustrated in FIG. 3, relating more particularly to a tunnel on-board the vehicle of said system and within which said light source and light receiver are arranged.

FIG. 5 illustrates, in a schematic sectional view, the detail of FIG. 4, the light source and the light receiver being visible inside said tunnel.

FIG. 6 illustrates, in a schematic top view, the light source and the light receiver implemented in the system of FIGS. 3 to 5.

BEST WAY TO IMPLEMENT THE INVENTION

Figure 1:
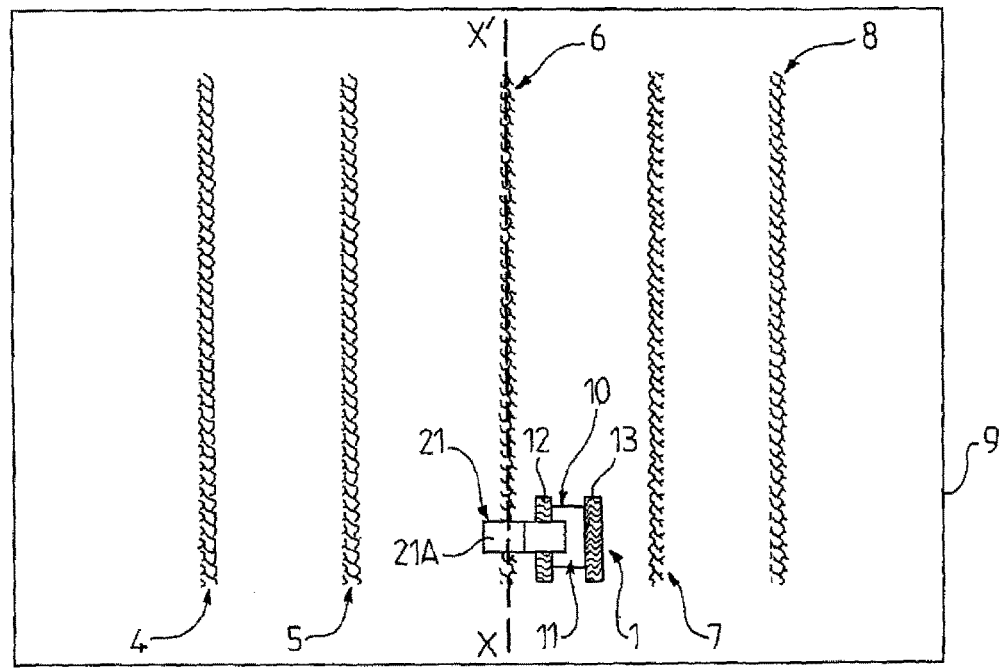
FIG. 1 illustrates, in a schematic top view, a vine plot grown in rows, with the vehicle of a system according to the invention in progression between two rows to characterize the physiological state of the woody plants composing one of said two rows (herein located on the left of the vehicle from the point of view of an observer positioned in front of FIG. 1).
Figure 2:
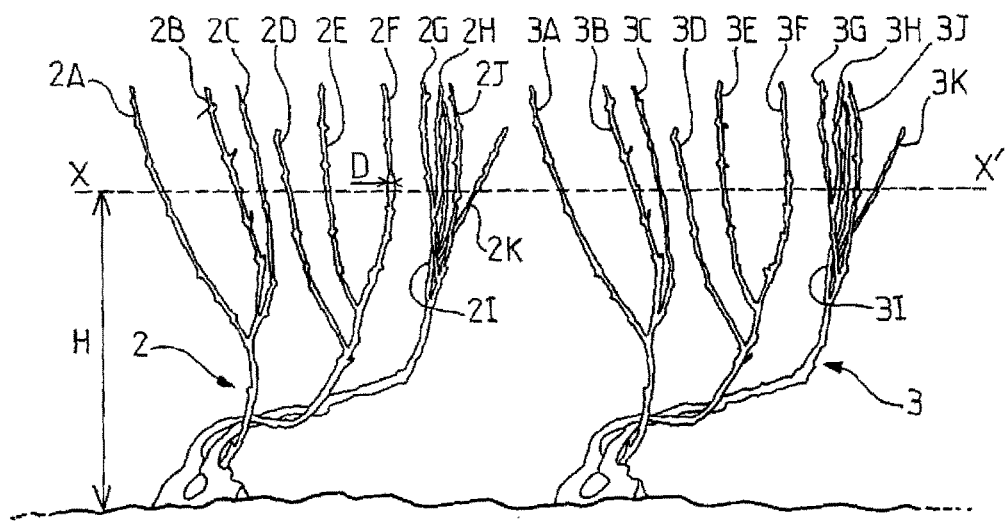
FIG. 2 illustrates, in a schematic elevation view, two vine plants belonging to one of the rows of the plot illustrated in FIG. 1, a dotted line symbolizing the direction of progression of the vehicle of the system according to the invention, this dotted line being placed at an altitude corresponding substantially to that at which the light source and light receiver are arranged.

The invention relates, according to a first aspect, to a system 1 for characterizing the physiological state of woody plants 2, 3, with branches 2A, 2B, 2C, 2D, 2E, 2F, 2G, 2H, 2I, 2J, 2K, 3A, 3B, 3C, 3D, 3E, 3F, 3G, 3I, 3H, 3J, 3K grown in rows 4, 5, 6, 7, 8, of the vine or fruit-tree type. Preferably, as illustrated in the Figures, said rows 4, 5, 6, 7, 8 are arranged parallel to each other, with an inter-row gap that is advantageously substantially constant over the whole concerned plot 9. Each concerned row 4, 5, 6, 7, 8 is formed of plants arranged in rows, one behind each other, and potentially comprises a system of staking and/or tying intended to form a structure to support the woody plants forming the rows 4, 5, 6, 7, 8 and to orient their growth.

Preferably, the characterizing system 1 according to the invention is specially adapted to characterize the physiological state of vine plants grown in rows in a plot 9 of a vineyard. However, the invention is not limited to characterizing the physiological sate of vine plants, and may alternatively relate to any other type of woody plants with branches (fructiferous or fruit tree, small tree or shrub, vegetables, etc.).

The characterizing system 1 according to the invention is a proxidetection system and comprises a vehicle 10 designed to progress between said rows 4, 5, 6, 7, 8, along a direction of progression X-X', which is herein substantially parallel to the rows 4, 5, 6, 7, 8, between which the vehicle 10 is caused to progress. Of course, the lateral dimension of the vehicle 10 is advantageously conformed so as not to exceed the width of the inter-row free gap. Within the framework of a vineyard, this width is for example substantially lower than or equal to 3 meters, and often lower than or equal to 2 meters, or event 1.50 meters. The vehicle 10 is preferably a terrestrial vehicle resting on the ground of the plot 9 and provided with at least one engine and ground-contact members allowing it to move on the ground of the plot 9 between the rows 4, 5, 6, 7, 8. Advantageously, the vehicle 10 comprises a motorized frame 11 with wheels, or still more preferentially caterpillars 12, 13. The use of caterpillars 12, 13 is preferred to allow the vehicle 10 to easily move, including on uneven or muddy grounds. Preferably, the vehicle 10 comprises a full track, for example of the Niko HY22® type, provided with a hydrostatic transmission, propelled by a thermal engine (gasoline) and equipped with a battery 12V connected to an alternator. The invention is of course not limited to a full track, and other types of vehicle can be contemplated (high clearance tractor or any other machine able to progress in a plot grown in rows), without thereby departing from the framework of the invention.

The system 1 according to the invention also comprises a geolocation device 14 on-board said vehicle 10 and designed to determine substantially continuously and in real time the instantaneous geographical position of the vehicle 10. Advantageously, the geolocation device 14 includes a receiver of a satellite positioning system, as for example a GPS receiver. The invention is however not limited to a specific geolocation means, even if a satellite positioning system is preferred. In this respect, the use of a GPS receiver is of course not the single contemplatable possibility within the framework of the invention. It is for example contemplatable to implement, instead of a GPS receiver forming a geolocation device 14, a Glonass receiver (Russian satellite geolocation system) or a Galileo receiver (European satellite geolocation system), or a GNSS receiver ("Global Navigation Satellites System"), which is a satellite geolocation system combining the three above-mentioned systems (GPS, Glonass and Galileo). For example, the geolocation system 14 is formed by a GPS receiver of centimeter accuracy (error lower than 2.5 cm per position) of the trademark Trimble® (for example, the model Ag332 RTK or Ag432 RTK radio), preferably able to deliver a parameterizable NMEA frame, with, for example, an output frequency of 1 Hz, 5 Hz, 10 Hz or 20 Hz. As will be explained in more detail hereinafter, the function of the geolocation device 14 on-board the vehicle 10 is to allow the location in space of the whole information collected by the system 1, in order in particular to establish maps of physiological variabilities of the woody plants (preferably formed by vine plants) composing the considered plot 9.

The characterizing system 1 according to the invention also comprises a processing unit 15 functionally connected to at least the geolocation device 14. The processing unit 15 is advantageously also on-board the vehicle 10, but it is perfectly contemplatable that it is not and is for example arranged permanently in a building or in another vehicle. The functional link between the processing unit 15 and the geolocation device 14 may be a wire-based link (as illustrated in the figures) or a wireless link. The processing unit 15 is advantageously provided with digital data processing and storage means, these processing means including for example a motherboard, a processor, one or several memories (RAM and/or ROM) and one or several peripheral units for storage (hard disk, whatever its technology: memory card, USB stick or other) and control. The processing unit 15 is advantageously provided with wire-based communication means allowing it to be connected to an on-board computer system via a wire-based transmission line (for example, of the following types: RS232, RS485, Bus I2C, Bus CAN, ProfiBus, ISOBus, UART, SPI type synchronous series link or compliant, or any other), or via a short, mean or wide range wireless transmission link (for example, infrared link, coupled or not to a standard of the IrDa type—RFID link, standard RF 433 MHz, 868 MHz, 2.4 GHz—RF coupled to a standardized protocol of the ZigBee, Bluetooth WiFi, Wimax type—long range RF of the GSM, GPRS, 3G, 4G type—satellite link . . . ). The processing unit 15 may for example be formed by a computer, preferably of the "hardened PC" type, in the case where the processing unit 15 is on-board the vehicle 10 and hence subjected to the use constraints of the latter.

The processing unit 15 may advantageously be formed by an on-board processing system of the tablet or smartphone type, integrating a suitable operating system and a software allowing to implement the method according to the invention. This processing system may advantageously be coupled to one or several additional memory cards supplementing the functions of said system and specializing them for the application.

The processing unit 15 may for example be alternatively formed by an on-board processing system architectured about an electronic on-board processing card of the market, coupled to one or several additional cards supplementing the functions thereof and specializing it for the application.

According to still another alternative, the processing unit 15 may for example be formed by an on-board processing system specifically designed for the application and architectured about one or several microprocessors, microcontrollers, processors of the DSP type, circuits of the SOC (System On Chip) type, PSOC, SOPC, programmable logic circuit (FPGA, CPLD type), specific application circuit (ASIC, Gate Array type). This specific card may be coupled or not to one or several additional cards supplementing the functions thereof and specializing it for the application.

According to the invention, the system 1 moreover comprises a sensor 16, shown as such in FIG. 6, said sensor 16 being preferably fully on-board the vehicle 10 to collect, as the vehicle 10 progresses along the direction of progression X-X', information relating to the physiological state of woody plants 2, 3 composing at least one of the two rows 6, 7 between which the vehicle 10 travels. More precisely, the sensor 16 includes a light source 17 designed to emit a light beam 18 and a light receiver 19 designed and arranged to pick-up, in the absence of obstacle between the light source 17 and the light receiver 19, the totality of the light beam 18. The light receiver 19 is hence advantageously mounted opposite the light source 17, so as to be hit by the light beam 18 emitted by the light source 17.

According to the invention, the light source 17 and receiver 19 are mounted on the vehicle 10 (i.e. on-board the latter) so as to be able to be arranged on either side of a row 6, in order that said light beam 18 can intersect, as the vehicle 10 progresses along said row 6, branches 2A-K, 3A-K, belonging to the woody plants 2, 3 of said row 6. The light source 17 and receiver 19 are hence designed to progress on either side of a given row 6, along the direction of progression X-X', so that the light beam 18 sweeps, at an altitude H, the branches 2A-K, 3A-K, of the woody plants 2, 3 composing the concerned row 6. As can be seen in particular in FIG. 6, the light beam 18 has, in the direction of progression X-X', a dimension L that is substantially greater than the diameter D of the thickest of the branches 2A-K, 3A-K of said row 6 interposed between the light source 17 and the light receiver 19, so that the interposition of a branch 2A between the light source 17 and receiver 19 cuts only partially said light beam 18 and hence projects on said light receiver 19 a shadow 20A from which the processing unit 15 determines, preferably immediately (on the fly), the local diameter D1 of the concerned branch 2A. It is moreover perfectly contemplatable, as illustrated in FIG. 6, that the light beam 18 intersects substantially simultaneously several branches 2A, 2B, so that several shadows 20A, 20B are projected on the light receiver 19, from which the processing unit 15 determines the respective diameters D1, D2 of the concerned branches 2A, 2B, as well as preferably the number of branches 2A, 2B intersecting the beam 18.

Thanks to this characteristics, it is possible to determine directly and in real time the local diameter (i.e. measured at the altitude H, along the fictive line materializing the direction of progression X-X') without it is required for that purpose to know the speed of progression of the vehicle 10, wherein the latter can be variable as a function of the nature of the ground of the plot 9 to be covered. The invention is hence based in particular on the idea to use a wide-enough beam 18 so that the dimension in the direction of progression X-X' of the shadow 20A resulting from the illumination of the branch 2A by the light beam 18 is correlated with the local diameter D1 of the branch 2A, independently of the speed of progression of the vehicle 10. In order to derive the local diameter D1 of the concerned branch 2A from the dimensions of the shadow 20A resulting from the illumination, by the light beam 18, of the branch 2A in question, the sensor 16 advantageously includes calculation means, comprising for example a microprocessor, one or several calculation programs, etc. The invention hence allows an independent measurement of the speed of progression of the vehicle 10.

The system 1 is advantageously designed so that the light beam 18 illuminates permanently the light receiver 19 by being only partially (and temporarily) blocked out by the branches 2A-K, 3A-K intersected as the vehicle 10 progresses along the concerned row 6, which allows to determine in real time and sequentially the local diameter D1, D2 of each of the concerned branches, at a given altitude H. Advantageously, the processing unit 15 is functionally connected to the sensor 16 so as to collect and store, by any suitable means (hard disk, memory card, etc.), the different values of local diameters determined by means of the sensor 16 as the vehicle 10 progresses along the concerned row 6. The processing unit 15 is further designed to associate with said diameter D1 of the concerned branch 2A information of geolocation of said branch 2A coming from the geolocation device 15. In other words, the processing unit 15 allows not only to collect and store the geolocation information produced by the geolocation device 14, but also to associate this geolocation information to the dimensional data D1, D2 coming from the sensor 16, in order to geolocate each branch local diameter measurement performed by the sensor 16, so as to be able to advantageously establish a map of the plot 9 allowing to visually assess the variability of the diameter of the branches 2A-K, 3A-K, at a given measurement altitude H. In the case where the plot 9 is a vine plot composed of vine plants, the characterizing system 1 according to the invention hence advantageously allows to automatically and continuously measure characteristic elements of each vine plant, allowing to accede indirectly to a piece of information on the vitality and the expression of the vegetative power of the vine. The system 1 hence allows in a way to "scan", by mean of the sensor 16, the vine rows 4, 5, 6, 7, 8, in order to measure the local diameter of each of the branches 2A-K, 3A-K, and to associate with each measured local diameter geolocation coordinates coming from the geolocation device 14. For example, the processing unit 15 is designed to concatenate the NMEA frame (or any other type of frame such as the raw data for example) of the geolocation device (when the latter is for example based on the GPS system) and the data obtained from the sensor 16, to obtain concatenated data that are preferably subsequently recorded, for example as a text file, in a memory card (such as a SD card, or any other storage medium as a USB stick, for example) for a subsequent map processing.

Advantageously, the characterizing system 1 is specifically designed to measure the local diameters D1, D2 of naked branches 2A, 2B, i.e. with no leaves, and still more preferentially of pruned naked branches (or woods or shoots) (pruning wood).

In the preferential embodiment illustrated in the Figures, where the system 1 is specifically designed to characterize the physiological state of a vine, the sensor 16 is specifically sized and positioned on the vehicle 10 so that its beam intersects the naked shoots and, still more preferentially, the pruned naked shoots. In this preferential application, the light beam 18 has, in the direction of progression X-X', a dimension L that is substantially higher than or equal to 30 millimeters, and still more preferentially, 26 millimeters, it being understood that a shoot generally does not exceed 25 millimeters in diameter. Advantageously, the processing unit 15 is designed to also determine the number of branches 2A-K, 3A-K, intersected by said light beam 18 as the vehicle 10 progresses, which allows for example to determine, in connection with the geolocation data, a number of branches (and more precisely, herein, of shoots) per surface unit.

Hence, the system 1 according to the invention allows to obtain very easily a substantially exhaustive count of the shoots present in a vine row 6, which allows to derive therefrom an indication about the vegetative expression. The system 1 according to the invention also allows to determine, preferably exhaustively, the unitary diameter of the pruning woods (i.e. shoots after the pruning), which gives an indication about the vitality of the vine. The possible measurements coming from staking/tying stems and other artefacts will be suppressed by the processing unit 15 by any suitable processing (thresholding, etc.).

Advantageously, the light source 17 is designed to emit a laser beam forming said light beam 18. The use of a laser beam as a light beam 18 proves particularly advantageous as far as the accuracy of measurement is concerned. The focused character of the laser beam indeed prevents the problems of accuracy liable to occur with conventional light beams (infrared beam, for example) that may have a great diffraction cone that is harmful for the accuracy of the measurements.

The invention is however absolutely not limited to the implementation of a light beam of specific nature, and it is perfectly contemplatable to use a light beam other than a laser beam if a lesser accuracy is acceptable.

Advantageously, the light beam 18 is in the form of a parallel flat brush, as illustrated in FIG. 6, said light beam 18 being advantageously a laser beam in the form of a parallel flat brush. Advantageously, the parallel flat brush in question has substantially a two-dimensional shape, and extends in a plane that is substantially parallel both to the direction of progression X-X' and to the ground on which are planted the rows 4, 5, 6, 7, 8 of the concerned plot 9. The light beam 18 has hence in this case substantially the shape of a rectangular plate, constituting a light barrier that each branch 2A-K, 3A-K comes to temporarily and partially block out as the vehicle 10 progresses along the row 6 concerned by the measured.

The so-formed parallel flat brush is preferably continuous in the direction of progression X-X', so as to form a web of light illuminating in a substantially homogeneous manner the light receiver 19 over its whole length. The continuity of the flat brush allows to contemplate that the light receiver 19 has a high enough resolution, for example of the order of one tenth of millimeters, or one micrometer or more, to measure accurately the size of the projected shadow of the branches 2A-K, 3A-K, and in particular the size of the projected shadow of the smallest branches 2A-K, 3A-K. The web of light is preferably generated by a single emitter, and focused as a continuous web by means of an optical system, for example a set of mirrors and focusing lenses.

As an alternative, the parallel flat brush may be formed by a plurality of discrete laser beams, parallel to each other. In this case, the discrete laser beams are preferentially separated from each other by a distance lower than the diameter of the branch 2A-K, 3A-K, of smallest diameter, or even by a distance lower than one tenth, or one hundredth, of the diameter of said branch of smallest diameter.

Advantageously, the light receiver 19 comprises a CCD sensor (charge transfer device) that allows, in combination preferably with a light beam 18 formed by a laser beam, an excellent accuracy of measurement (for example of the order of a tenth of millimeter), independent of the quality of light stopped by the concerned branch 2A, 2B. The CCD sensor indeed allows to detect in a very accurate manner the edges of the branch 2A, 2B, by capturing the edge of the laser beam stopped by each branch 2A, 2B, rather than the transmitted volume of light, which allows to obtain an excellent accuracy of measurement.

Advantageously, the sensor 16 is formed by an optical micrometer, and still more preferentially by a laser optical micrometer, for example of the KEYENCE® trademark. In particular, the KEYENCE® optical micrometers of the IG series proves to be particularly adapted to the desired objectives.

Advantageously, the system 1 according to the invention comprises a tunnel 21 placed on-board said vehicle 10, or formed by the latter, within which are arranged said light source 17 and light receiver 19, said tunnel 21 being designed to locally cover the row 6 concerned by the measurements.

Advantageously, the tunnel 21 is provided, at at least one of its ends (and preferably at each of its two ends), with a blocking curtain designed to limit the penetration of the ambient light into said tunnel 21, while allowing the displacement of the tunnel 21 along said row 6 under the effect of displacement of said vehicle 10. The use of such a blocking curtain proves to be useful in case of strong sunlight that could affect the good operation of the sensor 16. In the case where the vehicle 10 is formed by a high clearance tractor, the elements of the sensor 16 are respectively arranged on each leg of the high clearance tractor; the tunnel is hence no longer necessary in this precise case, because its function is ensured by the body itself of the tractor in question, which forms in itself said tunnel; only the blocking curtain can advantageously be used in this case if necessary.

Advantageously, a support 210 for the sensor 16 is mounted on the motorized frame 11. Preferably, said support 210 forms said tunnel 21. For that purpose, the support 210 takes for example a general inverted U shape, with a core 21A having for example the shape of a substantially rectangular plate, from which extend two arms formed for example by two opaque lateral walls 21B, 21C. The core 21A of the U is intended to overhang the row 6 object of the characterizing measurements by the system 1, whereas the arms of the U are arranged on each side of said row 6 and carry respectively the light source 17 and the light receiver 19. In the case where the vehicle 10 is formed by a high clearance tractor, the arms of the above-mentioned inverted U are advantageously formed by legs of said tractor. In order to avoid that the sensor 16 is subjected to the ambient light (in particular when the latter is of strong intensity), which could prevent or distort the measurements, the front face of the support 21 is preferably closed by two flexible blocking panels 22, 23, which form said above-mentioned blocking curtain. Said flexible blocking panels 22, 23 are advantageously opaque and designed to be deformed locally at the passage of the branches 2A-K, 3A-K, to allow the continuous displacement of the support 21 along the row 6, while preserving a sufficient level of obscurity in the cavity delimited by the support 21. Advantageously, the rear face of the support 21 is also equipped with flexible opaque panels (not visible in the Figures) so as to maintain the level of darkness required for the good operation of the sensor 16. For example, the flexible blocking panels 22, 23 may each comprise a brush band with a terminal area 22A, 23A formed of a multitude of bristles, so that said brushes sweep laterally the branches, hence allowing a fluid and continuous displacement of the support 21 while maintaining the level of darkness required at the level of the sensor 16 arranged inside the support 21, in the inner volume V delimited by the latter.

Advantageously, the sensor 16 is mounted mobile in vertical translation on the vehicle 1, so as to be able to adjust the altitude H at which the branches 2A-K, 3A-K are liable to intersect the light beam 18.

The optimum altitude indeed varies as a function of the plots, according to the characteristic specific to the cultivated plant (species, age, morphology, etc.). For example, the light source 17 and the light receiver 19 are respectively mounted vertically sliding on vertical rails 24, 25 arranged opposite to each other, said vertical rails 24, 25 being for example respectively integral with the arms 21B, 21C of the support 210.

It is also contemplatable that, in addition to this adjustability of the position of the sensor 16 in the support 210, a means for adjusting the altitude of the support 210 as a whole is also provided to allow the adjustment of the altitude at which the support 210 is positioned, in order to adapt to specific configurations of the rows to be studied (presence of poles, tying, etc.).

The invention also relates as such to a method for characterizing the physiological state of woody plants 2, 3 with branches 2A-K, 3A-K grown in rows 4, 5, 6, 7, 8, of the vine or fruit-tree type, said method comprising the following steps:
  a sensor 16, including a light source 17 designed to emit a light beam 18 and a light receiver 19, is associated with a row 6, so that said light source 17 and light receiver 19 are arranged on either side of said row 6;
  said sensor 16 is moved along said row 6 along a moving direction X-X' so that said light beam 18 can intersect, as the sensor 16 progresses along said row 6, branches 2A-K, 3A-K belonging to woody plants 2, 3 of said row 6, said light beam 18 having, in the direction of progression X-X', a dimension L that is substantially greater than the diameter D of the thickest of the branches 2A-K, 3A-K of said row 6, so that the interposition of a branch 2A, 2B between the light source 17 and receiver 19 cuts only partially said light beam 18 and hence projects on said light receiver 19 a shadow 20A, 20B from which the local diameter of the concerned branch 2A, 2B is determined;
  information of geolocation of said concerned branch 2A, 2B is associated with said local diameter D1, D2.

Of course, the method according to the invention is advantageously implemented by means of the above-described system 1 according to the invention, so that the characterizing method according to the invention preferably corresponds to the use of a system 1 as described hereinabove. From then on, the elements of description exposed hereinabove in relation with the system 1 are also valid as regards the method.

Advantageously, the sensor 16 is displaced substantially continuously along said row 6, for example at an average speed comprised between 2 and 15 km/h, and preferably of the order of 5 km/h, the operations of determining the diameters of the branches 2A-K, 3A-K being performed on the fly, as the progression goes along. For that purpose, the sensor 16 is preferably formed, as mentioned hereinabove, by an optical micrometer, and preferably by a laser micrometer implementing a laser beam having the shape of a parallel flat laser beam and a CCD sensor.

The method further advantageously comprises a step of determining the number of branches 2A-K, 3A-K, intersected by the light beam 18, in order to be able to accede to information about the biomass and hence the vegetative expression of the vine (and of any other woody plants with branches grown in rows).

Advantageously, as still mentioned hereinabove, the method according to the invention is implemented whereas said woody plants 2, 3 are in period of vegetative rest and hence substantially with no leaves. For example, the method according to the invention is advantageously implemented during the winter, for example after said woody plants 2, 3 have been pruned. Preferably, the method can of course be implemented after the fall of the leaves but before the pruning. It proves that the counting of the pruned woods and the measurement of their diameters allows to obtain information correlated to the vitality and the vegetative expression of the concerned woody plants (vine or other). It is hence possible, thanks to the geolocation of the measurements, to map the plot 9, which proves to be extremely useful, in particular in the case of a vineyard, to implement suitable phytosanitary treatments and mechanical or manual cultural operations (fertilization, pruning . . . ) that take into account the intra- and inter-plot variability.

POSSIBILITY OF INDUSTRIAL APPLICATION

The invention finds an industrial application in the design, the manufacturing and the implementation of systems for characterizing the physiological state of plants.

The invention claimed is:
1. A system (1) for characterizing the physiological state of woody plants (2, 3) with branches (2A, 2B, 2C, 2D, 2E, 2F, 2G, 2H, 2I, 2K, 3A, 3B, 3C, 3D, 3E, 3F, 3G, 3H, 3I, 3K) grown in rows (4, 5, 6, 7, 8), of the vine or fruit-tree type, said system (1) comprising a vehicle (10) designed to progress between said rows (4, 5, 6, 7, 8) along a direction of progression X-X', and also comprising a geolocation device (14) on-board said vehicle (10) as well as a processing unit (15), said system (1) being characterized in that it comprises a sensor (16) including a light source (17) designed to emit a light beam (18) and a light receiver (19), said light source (17) and receiver (19) being mounted on said vehicle (10) so as to be able to be arranged on either side of a row (6), so that said light beam (18) can intersect, as the vehicle (10) progresses along said row (6), branches (2A, 2B, 2C, 2D, 2E, 2F, 2G, 2H, 2I, 2K, 3A, 3B, 3C, 3D, 3E, 3F, 3G, 3H, 3I, 3K) belonging to the woody plants (2, 3) of said row (4, 5, 6, 7, 8), said light beam (18) having, in the direction of progression X-X', a dimension (L) that is substantially higher than the diameter (D) of the greatest of the branches of said row (6), so that the interposition of a branch (2A, 2B, 2C, 2D, 2E, 2F, 2G, 2H, 2I, 2K, 3A, 3B, 3C, 3D, 3E, 3F, 3G, 3H, 3I, 3K) between the light source (17) and receiver (19) cut only partially said light beam (18) and hence projects on said light receiver (19) a shadow (20A, 20B) from which the processing unit (15) determines the local diameter (D1, D2) of the concerned branch (2A, 2B), said processing unit (15) being further designed to associate with said local diameter (D1, D2) of the concerned branch (2A, 2B) information of geolocation of said branch (2A, 2B) coming from the geolocation device (15).

2. The system (1) according to claim 1, in which said processing unit (15) is designed to determine the number of branches (2A, 2B, 2C, 2D, 2E, 2F, 2G, 2H, 2I, 2K, 3A, 3B, 3C, 3D, 3E, 3F, 3G, 3H, 3I, 3K) intersected by said light beam (18).

3. The system (1) according to claim 1 in which said geolocation device (14) includes a receiver of satellite positioning system, such as for example a GPS receiver.

4. The system (1) according to claim 1 in which said vehicle (10) comprises a motorized frame (11) with wheels or caterpillars (12, 13), on which is mounted a support (210) taking a general inverted U shape, with a core (21A) from which extend two arms (21B, 21C), the core (21A) of the U being intended to overhang said row (6), whereas the arms (21B, 21C) of the U carry respectively the light source (17) and the light receiver (19).

5. The system (1) according to claim 1 in which said light source (17) is designed to emit a laser beam forming said light beam (18).

6. The system (1) according to claim 1 in which said light beam (18) is in the form of a parallel flat brush.

7. The system (1) according to claim 1 in which said light receiver (19) comprises a CCD sensor.

8. The system (1) according to claim 1 and including a tunnel (21) placed on-board said vehicle (10), or formed by the latter, and within which are arranged said light source (17) and light receiver (19), said tunnel being designed to cover locally said row (6) and being provided, at least one of its ends, with a blocking curtain designed to limit the penetration of the ambient light into said tunnel (21), while allowing the displacement of the tunnel (21) along said row (6) under the effect of the displacement of said vehicle (10).

9. The system (1) according to claim 1 in which said sensor (16) is mounted mobile in vertical translation on said vehicle (1).

10. The system (1) according to claim 1 in which said sensor (16) is formed by an optical micrometer.

11. A method for characterizing the physiological state of woody plants (2, 3) with branches (2A, 2B, 2C, 2D, 2E, 2F, 2G, 2H, 2I, 2K, 3A, 3B, 3C, 3D, 3E, 3F, 3G, 3H, 3I, 3K) grown in rows (4, 5, 6, 7, 8), of the vine or fruit-tree type, said method comprising the steps of:

providing sensor (16), including a light source (17) designed to emit a light beam (18) and a light receiver (19), is associated with a row (6), so that said light source (17) and light receiver (19) are arranged on either side of said row (6);

displacing said sensor (16) along said row (6) along a direction of progression X-X' so that said light beam (18) can intersect, as the sensor (16) progresses along said row (6), branches (2A, 2B, 2C, 2D, 2E, 2F, 2G, 2H, 2I, 2K, 3A, 3B, 3C, 3D, 3E, 3F, 3G, 3H, 3I, 3K) belonging to the woody plants (2, 3) of said row (6), said light beam (18) having, in the direction of progression X-X', a dimension L that is substantially greater than the diameter D of the thickest of the branches (2A, 2B, 2C, 2D, 2E, 2F, 2G, 2H, 2I, 2K, 3A, 3B, 3C, 3D, 3E, 3F, 3G, 3H, 3I, 3K) of said row (6), so that the interposition of a branch (2A, 2B, 2C, 2D, 2E, 2F, 2G, 2H, 2I, 2K, 3A, 3B, 3C, 3D, 3E, 3F, 3G, 3H, 3I, 3K) between the light source (17) and receiver (19) cuts only partially said light beam (18) and hence projects on said light receiver (19) a shadow (20A, 20B) from which the local diameter D1, D2 of the concerned branch (2A, 2B) is determined; and associating information of geolocation of said concerned branch (2A, 2B) with said local diameter D1, D2.

12. The method according to claim 11, in which said sensor (16) is displaced substantially continuously along said row (6).

13. The method according to claim 11 in which said sensor (16) is formed by an optical micrometer.

14. The method according to claim 11 and including the step of determining the number of branches intersected by said light beam.

15. The method according to claim 11 in which said method is implemented whereas said woody plants (2, 3) are still in period of vegetative rest and hence substantially with no leaves, for example during the winter.

* * * * *